United States Patent
Brodbeck (10) Patent No.: US 10,864,061 B2
(45) Date of Patent: Dec. 15, 2020

(54) SYSTEM FOR THE IN SITU CLEANING OF DENTAL IMPLANTS

(71) Applicant: Zyfoma GmbH, Weiterstadt (DE)

(72) Inventor: Urs Brodbeck, Erlenbach (CH)

(73) Assignee: Zyfoma GmbH, Weiterstadt (DE)

( * ) Notice: Subject to any disclaimer, the term of this patent is extended or adjusted under 35 U.S.C. 154(b) by 0 days.

(21) Appl. No.: 15/503,640

(22) PCT Filed: Aug. 13, 2015

(86) PCT No.: PCT/EP2015/068705
§ 371 (c)(1),
(2) Date: Feb. 13, 2017

(87) PCT Pub. No.: WO2016/023998
PCT Pub. Date: Feb. 18, 2016

(65) Prior Publication Data
US 2017/0265968 A1    Sep. 21, 2017

(30) Foreign Application Priority Data
Aug. 15, 2014    (DE) .......................... 10 2014 216 294

(51) Int. Cl.
*A61C 8/02*    (2006.01)
*A61C 8/00*    (2006.01)
(Continued)

(52) U.S. Cl.
CPC .......... *A61C 8/0007* (2013.01); *A61C 8/0089* (2013.01); *A61C 17/02* (2013.01);
(Continued)

(58) Field of Classification Search
CPC ..... A61C 8/0007; A61C 8/0089; A61C 8/006; A61C 17/0202; A61C 17/036;
(Continued)

(56) References Cited

U.S. PATENT DOCUMENTS 3,918,440 A    11/1975   Kraus
5,201,656 A *  4/1993   Sicurelli, Jr. ............ A61C 3/06
                                                 433/166
(Continued)

FOREIGN PATENT DOCUMENTS

CA    2891376 A1 *  5/2014   ........... A61C 8/0093
CH    561548 A5    5/1975
(Continued)

OTHER PUBLICATIONS

International Search Report received in PCT/EP2015/068705, dated Nov. 9, 2015.
(Continued)

*Primary Examiner* — Sean M Michalski
*Assistant Examiner* — Shannel N Wright
(74) *Attorney, Agent, or Firm* — Suzannah K. Sundby, Esq.; Canady + Lortz LLP (57) ABSTRACT

Disclosed herein is a cleaning system (30) for a dental implant part (2) that has been introduced into the jaw bone of a patient. For this purpose, in an advantageous embodiment of the invention, a securing element, which is adapted on the end side to connect to a corresponding connection element in the dental implant part, particularly preferably which can be screwed into a thread of the dental implant part by the end side, and to which a distribution element for a cleaning fluid as well as an electrical contact element can be attached, which distribution element can be connected to an external media reservoir via a media channel, and via which electrical contact element, a power source that is connectable to an external power source can be electrically connected to the dental implant part.

21 Claims, 4 Drawing Sheets (51) Int. Cl.
*A61C 19/06* (2006.01)
*A61C 17/02* (2006.01)
*A61C 17/00* (2006.01)
*A61N 1/05* (2006.01)
*A61N 1/32* (2006.01)

(52) U.S. Cl.
CPC ........ *A61C 17/0202* (2013.01); *A61C 17/036* (2013.01); *A61C 19/063* (2013.01); *A61N 1/0548* (2013.01); *A61N 1/325* (2013.01)

(58) Field of Classification Search
CPC ..... A61C 17/02; A61C 19/063; A61C 19/002; A61C 8/0093; A61N 1/0548; A61N 1/325
USPC .............. 433/32, 80; 601/162–165; 210/764; 606/32–52
See application file for complete search history.

(56) References Cited

U.S. PATENT DOCUMENTS

| | | | | |
|---|---|---|---|---|
| 6,419,868 | B1* | 7/2002 | Johnson | A61N 1/0568 264/249 |
| 2005/0256540 | A1* | 11/2005 | Silver | A61C 8/00 607/3 |
| 2008/0138761 | A1* | 6/2008 | Pond | A61C 5/40 433/29 |
| 2010/0298886 | A1 | 11/2010 | Kraus et al. | |
| 2012/0028215 | A1* | 2/2012 | Wade | A61C 8/0089 433/75 |
| 2012/0156645 | A1* | 6/2012 | Jacoby | A61C 8/0062 433/173 |
| 2012/0196251 | A1* | 8/2012 | Taft | A61B 18/1402 433/216 |
| 2013/0166039 | A1* | 6/2013 | Shaw-Klein | A61C 8/0007 623/23.49 |
| 2014/0295373 | A1* | 10/2014 | Braegger | A61C 19/063 433/82 |
| 2015/0282907 | A1* | 10/2015 | Zipprich | A61C 8/0093 433/32 |

FOREIGN PATENT DOCUMENTS

| | | | | |
|---|---|---|---|---|
| CN | 103027757 A | 4/2013 | | |
| DE | 102012022593 B3 | 3/2014 | | |
| KR | 20100056051 A | 5/2010 | | |
| WO | 2007051339 A1 | 5/2007 | | |
| WO | 2009083086 A2 | 7/2009 | | |
| WO | WO 2014075755 A1 * | 5/2014 | ........... | A61C 8/0093 |
| WO | WO-2014075755 A1 * | 5/2014 | ........... | A61C 8/0093 |

OTHER PUBLICATIONS

Written Opinion received in PCT/EP2015/068705, dated Nov. 9, 2015 (Machine translation).
English Translation of International Preliminary Report on Patentability received in PCT/EP2015/068705, dated Feb. 16, 2017.
Office Action received in CN 201580054470.9 dated Nov. 28, 2018.

* cited by examiner

SYSTEM FOR THE IN SITU CLEANING OF DENTAL IMPLANTS

The invention relates to a cleaning system for a dental implant part that has been introduced into the jaw bone of a patient.

To compensate for the loss of a tooth, dental implants can be used within the frame-work of the reconstructive therapy. Usually, they are inserted into the jaw bone in the place of an extracted or shed tooth, in order to fix there, after a healing-in phase of about four to twelve weeks, a prosthetic part or a crown serving as a denture piece. For this purpose, such a dental implant is usually designed as a suitably shaped metallic body, which is inserted in the intended place in the jaw bone by screwing it in. As a rule, the apical end of the dental implant is provided with a screw thread, mostly a self-cutting screw thread, with which the dental implant is inserted into the correspondingly prepared implant bed.

Such dental implants can be designed in single-part or else in multi-part construction. In the multi-part construction, such a dental implant usually comprises a first dental implant part, also referred to as post part or implant properly speaking, which is inserted into the patient's jaw bone by screwing it in, in the intended place, and includes, consequently, the suitable screw thread, in most cases a self-cutting screw thread, in its outer region. This first dental implant part is usually provided with suitable means for creating a connection to a second dental implant part to be added subsequently, which means are intended for supporting the prosthetic part properly speaking for the patient. To create the before-mentioned connection between these implant parts, usually a screw connection is used, the inner region of the first dental implant part to be inserted into the jaw bone including as connection means an internal thread into which a connecting screw can be screwed. The second implant part is then secured on the first dental implant part via such a connecting screw.

Such a multi-part design of the implant usually offers the advantage that the treatment of the patient can be subdivided into several treatment and processing steps, so that individual treatment sections can be kept relatively short and, therefore, sparing for the patient. Usually, in a first treatment step, the first dental implant part is inserted, i.e. screwed, into the jaw bone and allowed to heal in after the insertion for a certain period of time, for example, six weeks. In the meantime, the second dental implant part, usually also referred to as abutment, can be prepared for its subsequent insertion, and the prosthetic part can suitably be adapted, prepared or manufactured, taking into account, for example, the geometric parameters and the like. After termination of the first healing-in phase, the abutment or second dental implant part can be secured on the post part or first dental implant part, in a second treatment step, by means of the connection means provided, i.e. as a rule via a connecting screw, and afterwards, the prosthetic part can be placed onto the abutment with a precise fit.

In view of the meanwhile relatively high number of implants inserted into the human body and their relatively long duration of use, it has been noted that the occurrence of biofilm-associated inflammation statuses of the periimplantary tissue is constantly increasing. Namely, on the solid surface of the implant enclosed by tissue and tissue liquid, a biofilm develops, which is colonized by bacteria, which may finally lead to chronic and recurrent infections. This syndrome is called periimplantitis. In particular in the dental region, similar to periodontitis, a combination of neglected mouth hygiene, adhesion of a biofilm on the usually micro-rough surface of the post part and other factors lead to the full picture of periimplantitis, which is characterized by an increasing charge and destruction of the hard and soft tissues. The regions where the hard and/or soft tissues retreat are usually covered by a biofilm.

Both with and without treatment, a progressing of the periimplantary inflammation may lead to loss of the implant and deterioration the tissue of the body or bone in the region of the anchoring spot. Therefore, it is desirable to initiate suitable countermeasures as soon as possible after discovering such an inflammation. These measures may range from an optimization of the mouth hygiene to therapeutic interventions in the form of surgical measures, i.e. in particular removal of the afflicted implant and new insertion of a replacement implant. However, in particular the last-mentioned measure is a great burden for the tissue as a whole and often entails a massive reduction of tissue in the environment of the place of insertion. Therefore, it is highly desirable to find alternative efficient measures for fighting an existing or beginning periimplantitis.

From DE 10 2012 022 593, a concept for fighting or containing a beginning periimplantitis is known, with which the affliction by bacteria and the inflammation focuses, which may be the reason of the periimplantitis, can be fought in a particularly efficient manner. Surprisingly, it has turned out in this concept that an application of current or voltage pulses to the implant afflicted by the bacteria, in combination with a fluid-based treatment of the implant, is efficient to a particularly high degree for conditioning the implant and killing and removing the bacteria. In this way, it is in particular possible in a particularly efficient and reliable manner to remove organic residues, which after killing of the bacteria might still adhere on the material and undesirably promote a new colonization by bacteria.

The invention is based on the problem to provide a cleaning system for a dental implant part that has been introduced into the jaw bone of a patient, with which the reliable utilization of a combined cleaning concept, which is both electricity and fluid-based, is further simplified and, therefore, made particularly easily applicable.

This problem is solved according to the invention by a securing element which is adapted on the end side to connect to a corresponding connection element in the dental implant part, particularly preferably which can be screwed into a thread of the dental implant part by the end side, and to which a distribution element for a cleaning fluid as well as an electrical contact element can be attached, which distribution element can be connected to an external media reservoir via a media channel, and via which electrical contact element, a power source that is connectable to an external power source can be electrically connected to the dental implant part.

The invention starts out on the consideration that a particularly reliable and also broad-spectrum application of the above-mentioned combined cleaning concept is possible by keeping the handling of the cleaning system provided for this purpose, in particular its assembly and disassembly, particularly simple. In particular, the cleaning system should be of a design which can be assembled and disassembled so easily that it can even be applied to an implant part inserted in the patient's mouth, without subjecting the patient to unreasonable stress during the treatment. In the present case, it is desired to a particularly high degree to keep the final assembly particularly simple, so that the corresponding cleaning times in the patient's mouth can be kept relatively short.

To make this possible, it is provided to configure the cleaning system in several parts. On the one hand, the cleaning system comprises a securing element which is provided with suitable means for being secured on the dental implant part or post part inserted in the patient's mouth. The securing or connecting means in this sense can be, for example, a bayonet catch or the like. When applying the screw connections usually used for multi-part dental implants, the securing element is provided, particularly preferably on its end side, with a suitably dimensioned external thread adapted to the internal thread on the post part, so that the securing element can be screwed into the thread provided in the inserted dental implant part. The securing element can, therefore, be mounted on the inserted post part by simply screwing it in, which is a process that can be carried out relatively quickly and is simple to handle, thus entailing only little stress for the patient, in view of the otherwise relatively simple construction of the securing element.

Further components comprised by the cleaning system are one component for feeding the cleaning fluid and one component for creating an electrical current path via which the inserted dental implant part needing treatment can be connected with an external power source. To keep the final assembly for these components, too, and, therefore, for the cleaning system as a whole, particularly simple, these two components can be slipped on the securing element. The two components can be designed in this case as separate components or else, in the manner of an integrated construction, can each be part of one component, which, as such, can be slipped on the securing element.

Therefore, altogether, a cleaning system designed in this manner, allows a particularly simple final assembly, together with short processing times, because the screwing-in process, necessarily involving a rotational movement, is limited to a particularly simple and, thus, easy-to-operate component, namely the securing element, whereas the components of more complicated design, namely the electrical contact element and the distribution element for the cleaning fluid, which are each connected with feed lines, channels, wires or the like, and would, therefore, impede rotational movements, can be slipped on the securing element in axial direction and can, therefore, be mounted without significant interference of feed lines or the like.

According to the concept, the cleaning system is advantageously designed for subjecting the dental implant part, in its assembled state, to a combined treatment both on the basis of an application of electrical current and on the basis of a cleaning with a cleaning or rinsing fluid. It is in this case preferably provided to configure the dental implant part as an electrode in an electrical current path and to contact it accordingly with an external power source, so that the current flow provided for cleaning purposes can pass through the surface of the dental implant part. To allow this in a particularly simple manner, the securing element comprises in an advantageous embodiment an electrically conductive, preferably metallic, base body, which is provided with an electrically insulating surface coating. The region of the external thread, via which the securing element can be screwed into the dental implant part, shall, however, preferably have an uncoated, electrically conductive outer surface, so that an electrical contact between the securing element and the dental implant part can be produced by means of the engaging thread. That end of the securing element which is facing away from the dental implant part can suitably include an exposed electrically conductive and externally contactable partial surface via which the electrical contact with the contact element, and via the latter, with the external power source, can be produced. In this way, the electrical connection of the dental implant part to the external power source is possible via the securing element and the electrical contact element.

The distribution element is provided for feeding and distributing the cleaning fluid in the spatial area in the immediate environment of the dental implant part. For this purpose, the distribution element is preferably of an annular design and includes a media ring channel that is connectable on the media side with the media channel and is provided with a number of media outlet openings, i.e. one or more, which are preferably distributed over the periphery. Due to the annular design of the distribution element, the latter can be slipped on the dental implant part, while being attached onto the securing element, in the manner of a concentric positioning, in such a way that the media outlet openings are positioned around the outer periphery of the dental implant part, so that it is possible to apply cleaning fluid to the entire outer periphery of the dental implant part with. In order to enable a particularly targeted supply of the cleaning fluid, the distribution element is dimensioned and designed in a particularly advantageous embodiment in such a manner that the media outlet openings are located at a distance of maximally 10 mm, preferably maximally 5 mm, particularly preferably maximally 3 mm, from the external surface of the dental implant part. In view of the intended embodiment of the targeted electrical current control in the cleaning system mounted on the dental implant part, the distribution element includes in an expedient embodiment an electrically insulating external housing which is preferably made from a synthetic material.

In order to achieve a particularly reliable and efficient effect during the treatment of the dental implant part, it is provided in a particularly advantageous embodiment to guide the current or current pulse through the fed cleaning fluid and/or through the media channel provided therefor, when applying current to the dental implant part. This is based on the consideration that in a very particularly preferred embodiment, it is provided to use as cleaning fluid the cleaning fluid whose components and variants are known from DE 10 2012 022 593. The content disclosed there with regard to type and composition of the cleaning fluid as well as the latter's essential components and composition variants is herewith incorporated in its entirety Due to its fraction of salt or ions, such a cleaning fluid is electrically conductive, so that the fluid column inside the media channel can also be used as a current-carrying element, in the manner of an additional utilization. In case of this particularly preferred additional utilization of the fluid column, the current flows to the dental implant part, which, thus, serves as an electrode when current is applied, on the one hand through the power supply line, the electrical contact element and the securing element. On the other hand, the current flows, starting from the surface of the inserted dental implant part, through the cleaning fluid surrounding the latter and wetting its surface, the distribution element and the media channel through the fluid column present in said media channel. If necessary, a current-conducting cable may be integrated in the media channel in an advantageous embodiment, possibly for improving the electrical conduction properties, Due to the plug-type connection provided for mounting the cleaning system, i.e. for attaching the distribution element, on the one hand, and the electrical contact element, on the other hand, at or on the securing element,—in the manner of plugging them on—, the cleaning system is particularly well suited for a particularly simple final assembly in the patient's mouth. In order to further improve the simplicity and operating safety of the system, in view of the above, and to satisfy in particular the highest demands concerning hygiene and provision in the patients' treatment, the distribution element and/or the electrical contact element are designed as throw-away product(s) in a very particularly preferred embodiment, because it can be ensured especially by such an execution as throw-away products, which is considered as independently inventive, that without the highest demands of hygiene are satisfied without further safety measures, it being possible at the same time to keep the handling of the entire system particularly simple.

The execution as a throw-away product specifies in particular that the respective element is of a particularly inexpensive design and intended for one-time use only, with regard to the choice of the materials used and/or the production or processing methods applied. An element designed as such a throw-away product can in particular be designed, in a particularly preferred development, for its irreversible destruction during removal or disassembly of the cleaning system. It is in this way ensured that an undesired multiple use, which would necessarily require an expensive cleaning and disinfecting procedure, is excluded by the system itself. Such a design may presuppose in particular that the respective element cannot be disassembled in a nondestructive manner. This can be achieved, for example, by providing seals or envelopes or the like which are broken, torn or damaged in another manner during assembly or disassembly, so that the user can immediately recognize, already prior to the assembly, whether the element in question is an unused one.

In a particularly preferred embodiment, the media channel for the cleaning fluid opening out into the distribution element is provided on its inner surface with an electrically conductive, preferably metallic, coating. The latter can contribute, on the one hand, to the electrical conduction properties of the media channel and thus to the latter's proper functioning as an electrical current feed line. In a very particularly preferred embodiment, such a metallic coating can, on the other hand, also be provided as a metallic sacrificial coating, which is successively dissolved by the cleaning fluid during use of the respective distribution element, so that the respective ions are introduced into the cleaning fluid. This execution of a metallic coating as a sacrificial coating, which is also considered as independently inventive, enables, on the one hand, with particularly simple means an introduction of metal ions into the cleaning fluid during the latter's transport through the media channel, so that the enrichment of the cleaning fluid with ions necessary or intended for the cleaning on the place of treatment, i.e. on the surface of the inserted dental implant part, can be ensured. On the other hand, the execution of the coating as a metallic sacrificial coating, that is dissolved after a certain operating time, also guarantees independently and in a particularly simple manner the particularly preferably provided design of the respective components as a throw-away product, because once the sacrificial coating is "used up", the efficiency of the cleaning system is no longer readily given.

The embodiment of this metallic coating as a sacrificial coating, i.e. as a relatively thin coating, that disappears after a certain operating time due to the progressing embedding of ions into the cleaning fluid, enables thus in a particularly simple manner to design the distribution element as a throw-away product, because the proper functioning of the distribution element in accordance with the concept depends on the input of ions from the sacrificial coating into the cleaning fluid. Particularly preferably, such a sacrificial coating is provided in the form of a coating on pure titanium as basic material for the respective media channel.

The coating, which in the above-mentioned manner is preferably designed as a sacrificial coating, is particularly preferably designed according to the criteria that the coating material dissolves when the cleaning fluid is applied thereon, in order to supply the desired fraction of ions to the cleaning fluid and to enable the desired current flow. Furthermore, the materials of the sacrificial coating should be tolerable to the body, i.e. the released quantities should not develop any detrimental effects in the human body, and they should not deposit metallically on the implant body. Therefore, particularly preferably, the sacrificial coating comprises as components manganese, zinc and/or copper and/or, in a very particularly preferred embodiment, magnesium and/or aluminum.

Such an embodiment enables a particularly preferred use of the distribution element, which is considered as independently inventive, in combination with an electrolyte comprising citric acid, lactic acid, malic acid and/or ethanoic acid. This particularly preferred combined use creates, through the input of ions from the sacrificial coating into the electrolyte, the cleaning and treating fluid, which is actually effective in the inserted region of the implant and which comprises, in addition to the above-mentioned fractions of acids, the fraction of ions from magnesium, aluminum, potassium and/or calcium, and which is known, with regard to its components and variants, from DE 10 2012 022 593. Especially a cleaning fluid comprising these components has surprisingly turned out to be particularly reliable and effective in the treatment of the inserted implant part. Preferably, the electrolyte supplied to the distribution element can also contain from the start additional fractions of a metal salt comprising magnesium, aluminum, potassium and/or calcium ions.

In a method for cleaning an implant part from an adhering biofilm, which is also considered as independently inventive, an electrolyte, comprising citric acid, lactic acid, malic acid and/or ethanoic acid, is guided through a media channel provided with a metallic sacrificial coating and enriched at the same time with metal ions, particularly preferably with magnesium or aluminum ions, before a current flow is applied to the electrolyte enriched in this way with metal ions, using the implant part to be cleaned as an electrode.

Regarding the mechanical properties of the design of the plug-on connection for plugging the contact element and the distribution element onto the securing element, preferably a type of snap-in or clips connection is provided. In particular, the external housing of the distribution element advantageously includes a detent collar that can be attached to a corresponding peripheral bead of the securing element, whereas the electrical contact element includes in a particularly advantageous embodiment a contact clamping ring which is connected with the power supply line in an electrically conductive manner and which is provided with a number of contacting tips. Said contact clamping ring is preferably designed and dimensioned such that the contacting tips bend when they are attached or plugged onto the securing element, thus providing for a particularly reliable hold of the attached element on the securing element. This enables, on the one hand, a reliable electrical contacting between the contact element and the securing element, while, on the other hand, due to this bending, it is made possible in a particularly simple manner to design the contact element as a through-away product. The user can in particular recognize unambiguously and without any doubt, after one use of the contact element, due to the formed bending of the snap-in teeth or contacting tips, that the element in question has already been used and is, therefore, unsuitable for a renewed application.

Particularly preferably, some or all components of the cleaning system which are intended for carrying current are made from titanium (Ti), preferably pure titanium (grade 1 to 4), zirconium (Zr), tantalum (TI) or an alloy of some or all of these components as basic material, because this can be applied for the above-mentioned purposes in a particularly reliable manner, thanks to its high biocompatibility. In order to guarantee in this case in a simple manner a particularly high safety of operation, also in view of the preferably provided execution as a through-away product, these components are particularly preferably provided with a water-soluble outer coating made, for example, of sugar, in the manner of an encapsulated design, which outer coating dissolves when it gets into contact with the cleaning fluid or a body fluid, exposing the electrode material properly speaking. The outer coating can be applied directly on the basic material or, if necessary, also on the sacrificial coating provided thereon, in the manner of a stack of layers.

The advantages achieved with the invention consist in particular in the fact that the multi-part design of the cleaning system and the functional separation during assembly of the individual elements (rotational movement when screwing the securing element into the thread of the dental implant part on the one hand and axial plug-in movement when attaching the electric contact and distribution elements provided with wires, supply lines and the like) simplifies to a particularly high degree to mount the system even for inserted dental implant parts that have remained in the patient's mouth.

An exemplary embodiment of the invention is explained in detail by means of a drawing, in which FIG. 5 is a longitudinal sectional view of a contact element of the cleaning system according to FIGS. 3, 4 (FIG. 5A) and a top view thereof (FIG. 5B), FIG. 6 is a bottom view of a distribution element of the cleaning system according to FIGS. 3, 4 (FIG. 6A) and a longitudinal sectional view thereof (FIG. 6B)

Identical parts are marked with the same reference numbers in all figures.

Figure 1:
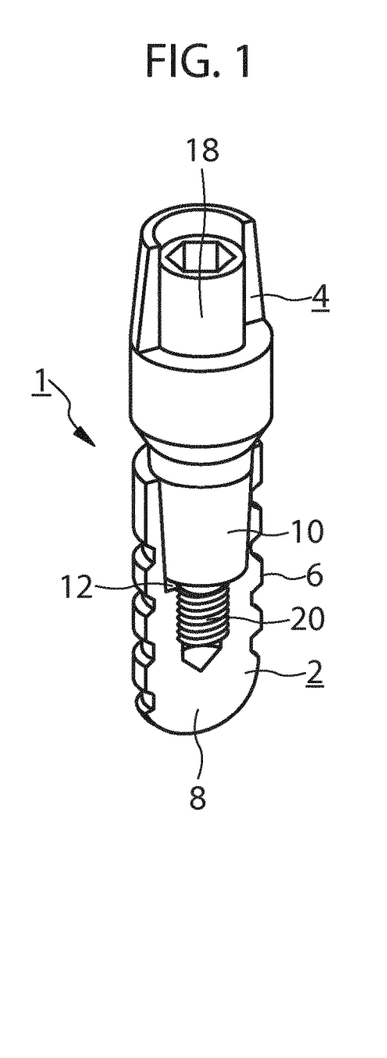
FIG. 1 shows a multi-part dental implant in assembled state.

The dental implant system 1 according to FIG. 1 is intended for use in the jaw bone in the place of an extracted or shed tooth, to fix there a prosthetic part or a crown serving as a denture piece. The dental implant system 1 is made up of several parts and comprises a first dental implant part 2 configured as a so-called post part, and a second dental implant part 4, also referred to as superstructure part or abutment, associated therewith and provided for attaching a denture piece. The first dental implant part 2 or post part is provided on its outside with an external thread 6, configured, in particular at the apical end 8, as a self-cutting screw thread, with which the first dental implant part 2 or post part can be inserted in the intended place in the jaw bone by screwing it in.

Figure 2:
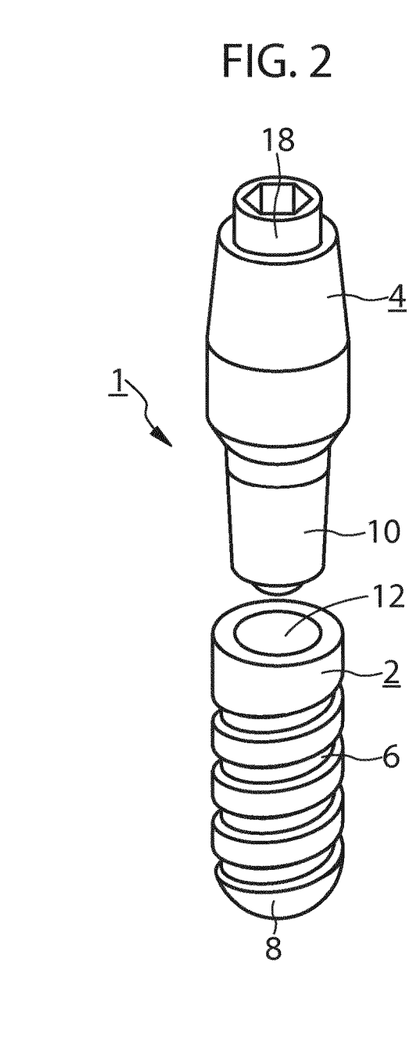
FIG. 2 is an exploded view of the dental implant according to FIG. 1.

In order to make it possible, after suitably securing the denture piece or the prosthesis on the abutment or second dental implant part 4, to anchor it in the post part or first dental implant part 2 with high mechanical stability, a connection stud 10 is moulded onto the second dental implant part 4, which connection stud 10 can be pushed into an associated receiving channel 12 provided in the first dental implant part 2. By pushing the connection stud 10 into the receiving channel 12, the implant parts 2, 4 are mechanically coupled with each other. To ensure a high mechanical stability, the outer contour of the connection stud 10 is adapted to the inner contour of the receiving channel 12, it being possible that both of them are of conical shape, viewed in longitudinal direction. Furthermore, the outer contour of the connection stud 10—and in according adaptation, the inner contour of the receiving channel 12—can be designed in cross-section with a multiple symmetry, so that, when joining the above-mentioned components, a rotational locking gear is created and thus, a reliable rotational orientation of the abutment relative to the post part can be adjusted.

The dental implant system 1 is provided with connection means for connecting the implant parts 2, 4 with each other. These connection means can in general be any connection means suitable for this purpose, such as, for example, a bayonet catch or the like. In view of currently common constructions of dental implants, a screw connection is provided in the exemplary embodiment as such connection means, in the manner of a particularly preferred embodiment. For this purpose, a connecting screw 18 is provided, which engages into a screw thread 20 provided inside the first dental implant part 2. With regard to the choice of their material, the implant parts 2, 4 are suitably adapted to the intended application and are in particular made of a suitably chosen metal, such as, for example, titanium.

In general, dental implant systems, in particular also two-part implant systems of the above-described type, present the problem that inflammations or inflammation focuses may arise due to a penetration of bacteria or germs into the tissue region near the place of insertion, in particular in the region of the external thread 6 cut into the jaw. Such inflammations, in particular also as a consequence of a so-called periimplantitis, may lead to a serious deterioration of the tissue and the bone in the region of the place of insertion, especially when they are able to develop and take hold over a long period. Without suitable countermeasures, these deteriorations may lead to the necessity to remove the entire implant system, i.e. in particular also the already inserted post part or first dental implant part 2, from the bone and to replace it by another prosthetics. This most undesirable effect caused by the periimplantitis may, therefore, lead to a total loss of the implant system, so that renewed surgical measures, such as, for example, scraping out the afflicted region in the jaw bone and treatment with a new implant system might become necessary. Such a removal may, furthermore, entail a loss of bone or other loss of tissue substance, which in the extreme case may even make a new treatment with another implant impossible. Such a necessity of a new treatment caused by a periimplantitis may occur even after relatively long periods after the first insertion of the implant system of, for example, up to several years or even decades.

The germs or bacteria observed in connection with a periimplantitis may in principle colonize the inside of the post part 2, but, as a rule, they preferably adhere directly on the surface of the post part 2 inserted into the jaw bone, in the region of contact with the surrounding tissue or bone material, i.e. in particular in the region of the external thread 6. In the region of the latter, the surface of the post part 2 can be provided with a roughening or the like, in order to particularly promote the growing-in into the tissue or the bone and to support the healing-in of the post part 2 after its insertion. Especially in the region of such a roughening of the surface, actually considered as particularly favorable for the implant system, however, the colonization by germs or bacteria may take place increasedly, the roughness making a specific removal of the existing germs or bacteria even more difficult.

Therefore, suitable countermeasures are urgently required, in order to be able, in case of a beginning or already existing periimplantitis and under preservation of the already inserted implant system, i.e. in particular of the already inserted post part 2, to efficiently combat the inflammation focus and to kill the germs that have penetrated, so that afterwards, sound tissue or sound bone substance can develop again in the region around the external thread 6. For this purpose, it is desirable, in addition to a specific killing of the germs or bacteria in the afflicted region, to also reliably remove their material residues and fragments from the spatial region concerned, so that then, the afflicted region can be filled again by sound tissue or bone material and an intimate connection between the outer surface of the post part 2 and the surrounding tissue or bone material can develop again. In addition, the biofilm formed by the bacteria layer, including the organic residues of killed bacteria, should reliably be removed.

Figure 3:
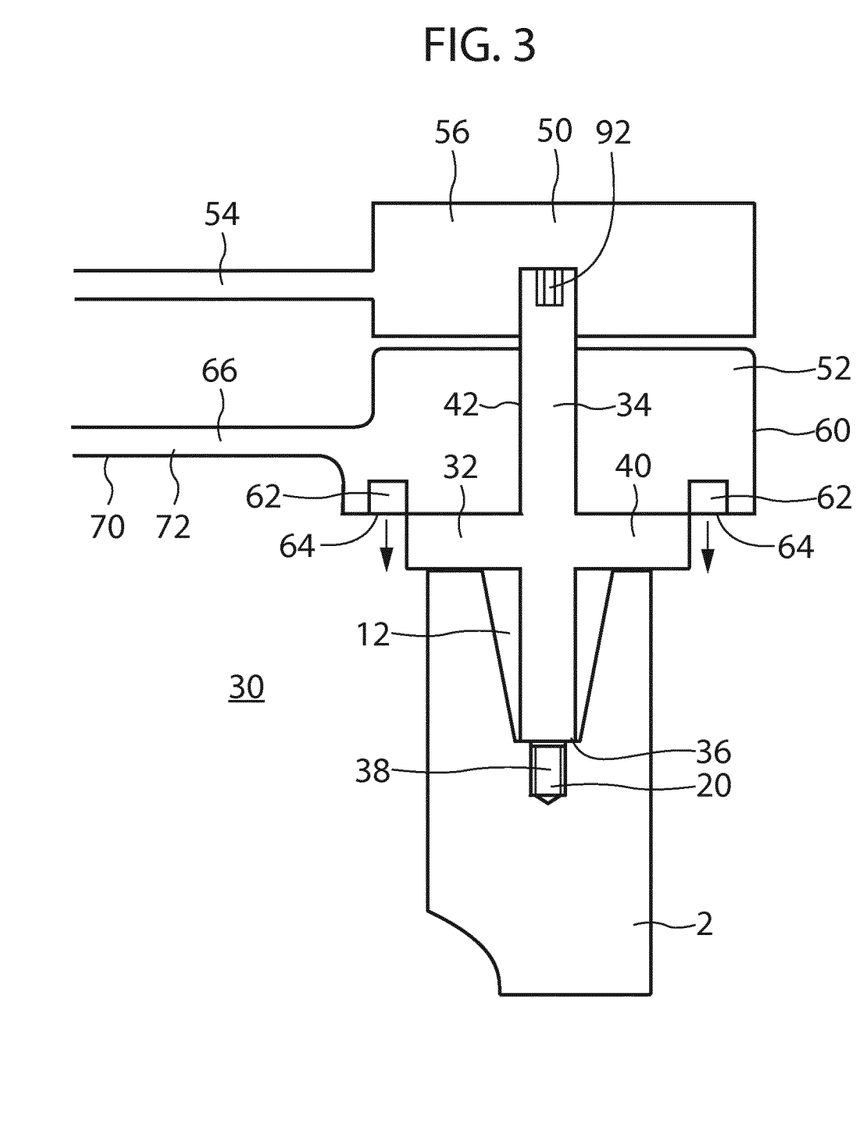
FIG. 3 is a longitudinal sectional view of a cleaning system for the post part of the dental implant according to FIGS. 1, 2, in assembled state.

For this purpose, i.e. for killing germs or bacteria in the insertion region of the post part 2 and in particular also for subsequently rinsing, removing and carrying away the residues of tissue and material of the killed bacteria, a treating or cleaning system 30 is provided, as is shown in FIG. 3 in a longitudinal sectional view and in FIG. 4 in an exploded view. The cleaning system 30 is specifically designed for treating the first dental implant part 2 or post part after having removed the second dental implant part 4 or abutment in the inserted state in the patient's mouth and to clean it from the colonization by germs or bacteria, by purposefully using a combined treatment of electrical charging with current, on the one hand, and applying a suitably chosen cleaning fluid, on the other hand. The cleaning system 30 is designed in this case for a particularly high ease of operation and assembly, so that the treatment time properly speaking in the patient's mouth can be kept particularly short and the stress for the patient can be kept particularly low.

Figure 4:
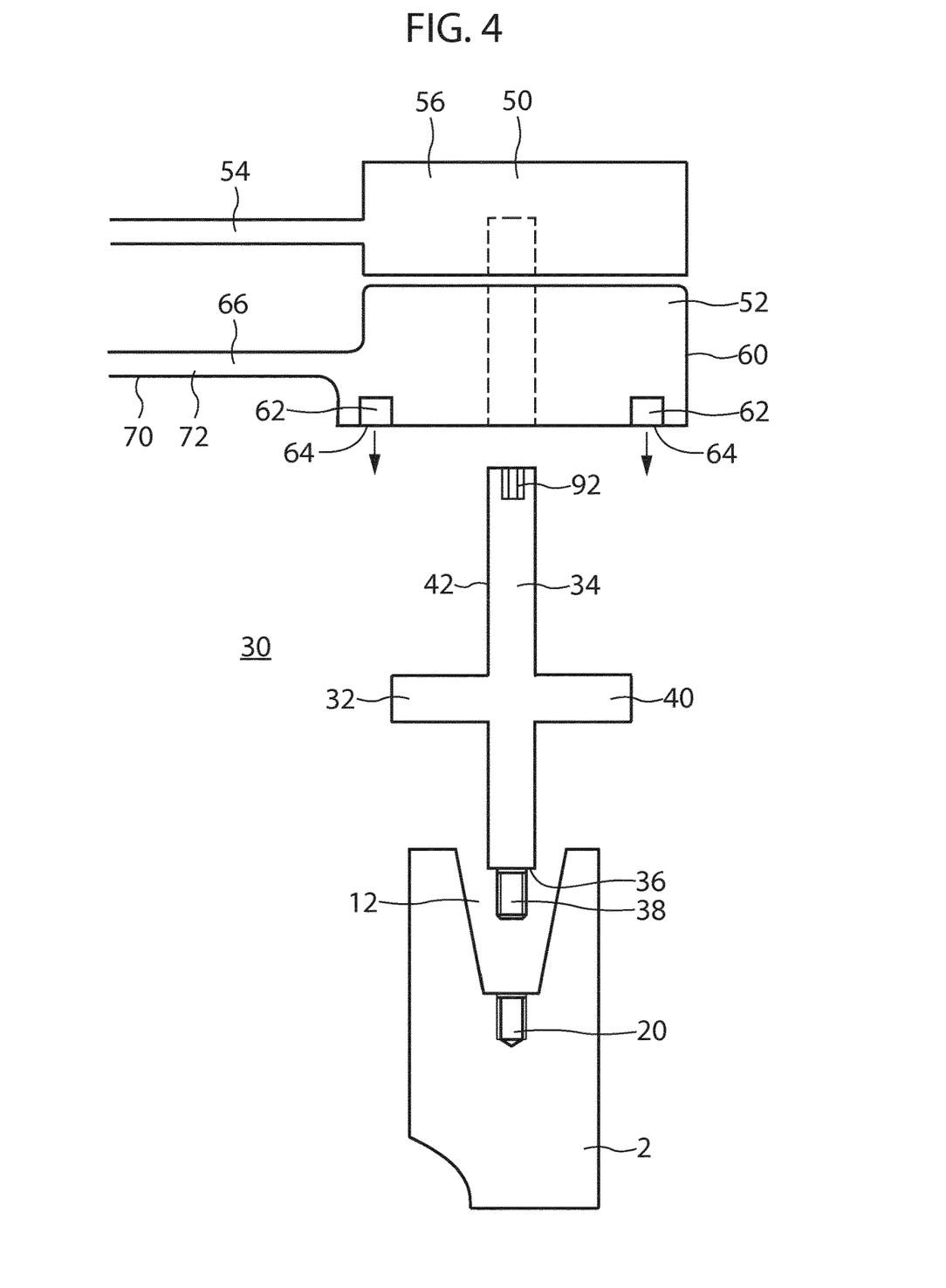
FIG. 4 is an exploded longitudinal sectional view of the cleaning system according to FIG. 3.

For this purpose, the cleaning system 30 is of a multi-part design, as can be seen in FIG. 3 and FIG. 4, the individual components being chosen such that a particularly high ease of assembly is given. The cleaning system 30 comprises in this case, on the one hand, a securing element 32 that is provided and designed for securing the other components on the inserted post part or first dental implant part 2. The securing element 32 comprises a base body 34 extending in longitudinal direction, in the exemplary embodiment of substantially cylindrical shape, whose end 36 is provided with an external thread 38. The external thread 38 is intended for being screwed into the screw thread 20 provided in the post part or first dental implant part 2 and is accordingly suitably adapted to the screw thread 20 with regard to its dimensioning, thread parameters and the like. As for the rest, the base body 34 is in the exemplary embodiment of a substantially cylindrical design and its dimensioning is chosen such that it can be pushed without problem into the receiving channel 12 actually provided for the connection stud 10. In principle, the base body 34 could also be of a conical design at its end area and thus be suitably adapted to the contour of the receiving channel 12.

To make it easier to screw the securing element 32 into the screw thread 20, a peripheral bead or annular bead 40 is arranged on the base body 34, which can be used as a handling aid for screwing in. To enable the electrical contacting of the post part intended for the purpose of applying current for the actual treatment of the post part or first dental implant part 2, the base body 34 of the securing element 32 is made from an electrically conductive material, in the exemplary embodiment a metallic material, and its exposed external surfaces are provided with an electrically insulating surface coating 42.

As for the rest, the securing element 32 is substantially free from further components, so that thanks to the simple construction, it is in particular possible to screw the securing element 32 into the screw thread 20 in a particularly easy way, without the interference of any bulky components. The securing element 32 serves in the assembled state for securing the further, active components of the cleaning systems 30, which can be attached to the securing element 32 for assembly in axial direction, as viewed from the base body 34. These components can, therefore, be mounted under avoidance of any turning or rotating movements, so that current or media lines exiting from the respective components interfere with the assembly or disassembly only slightly or not at all.

As active components for carrying out the cleaning properly speaking, an electrical contact element 50 and a distribution element 52 for a cleaning fluid are provided, both of which can be attached to the securing element 32 for a particularly simple assembly. In the exemplary embodiment, the contact element 50 and the distribution element 52 are designed as separate components; if needed and depending on the application in question, however, one integrated component could be provided, which contains these two elements in a common unit.

The electrical contact element 50 is connected to a power supply line 54 that can be connected to an external power source, which power supply line 54, in turn, can be connected via contact tongues, not shown in detail, which are suitably arranged in the contact head 56, with the metallic, electrically conductive base body 34 of the securing element 32 while the contact element 50 is attached on the securing element 32. In this way, an electrically conductive connection can be established from the external power source to the post part or first dental implant part 2 via the power supply line 54, the contact element 50 and the base body 34 of the securing element 32, while the securing element 32 is screwed into the post part 2 and the contact element 50 is attached to the latter.

The distribution element 52 is designed for delivering a cleaning fluid fed by an external media reservoir into the spatial vicinity of the post part 2 to be treated and for rinsing the latter's surface. Furthermore, the intended application of current during the treatment of the post part 2 shall be effected making use of the liquid column of the cleaning fluid as an electrical conduction element. For this purpose, the distribution element 52 comprises an electrically insulating external housing 60, which in the exemplary embodiment is made from a synthetic material. In the external housing 60, an annular media ring channel 62 is arranged, which includes a number of media outlet openings 64 arranged along the ring periphery in a distributed manner. The ring-channel structure is chosen in the exemplary embodiment in particular for the reason that the media ring channel 62 arranged in the housing 60 can be pushed onto the base body 34 of the securing element 32, so that in the assembled state of the cleaning system 30, the cleaning fluid can be efficiently applied to the external surface of the first dental implant part 2 over the entire periphery of the inserted post part 2.

As can be seen in FIG. 3, the media outlet openings 64 are positioned and arranged in the shown exemplary embodiment in such a manner that the exiting cleaning fluid flows along the outer surface of the inserted post part on the outside. Furthermore, that side of the base body 34 which in the assembled state is at the bottom is designed in the exemplary embodiment such that it rests on the upper end face of the inserted post part in an approximately level manner. In an alternative embodiment, these components can, however, also be configured such that the base body 34, viewed in peripheral direction, is positioned at least partially above the end face of the inserted post part 2, under formation of a gap, so that a medium can flow through. In such an embodiment, the base body 34 can, furthermore, be provided with through-channels through which the cleaning fluid, coming from the distribution element 52, can enter into the receiving channel 12, i.e. into the clearance between the inner surface of the post part 2 and the base body 34, so that it can also clean said base body 34. The cleaning fluid can then flow through the gap formed between the base body 34 and the end face of the post part 2 into the outer region of the post part 2 and can there take its cleaning effect in the above-described manner.

The media ring channel 62 is connected on the media side to a media channel 66 which, in turn, can be connected to the external media reservoir, possibly under insertion of pump arrangements or the like. The media ring channel 62 is, therefore, on the one hand, meant for the function of distributing the inflowing cleaning fluid around the post part or first dental implant part 2 as uniformly as possible, by means of the outlet openings 64 arranged in the periphery in a distributed manner. In view of the design concept of the cleaning system 30, namely that the post part or first dental implant part 2 shall be treated by a combined treatment through the cleaning fluid, on the one hand, and a current flow through its surface, on the other hand, the media-channel system for the cleaning fluid, comprising the media channel 66 and the media distribution ring 62, is, in addition, also designed for constituting the counter-electrode for the post part or first dental implant part 2. In the end region of the media supply, i.e. in particular in the region of the outlet openings 64, the current flow shall be made possible due to the electrical conductivity of the cleaning fluid itself. In order to design the required electrical contacting in a particularly reliable and also efficient manner, the media-channel system can additionally be designed in the manner of an electrode. For this purpose, a power cable may be integrated, on the one hand, into the media channel 66, the exposed, electrically conductive end of which can be positioned in the region of the media distribution ring 62. Alternatively or additionally, the inner surface of the media channel 66 and/or of the media distribution ring 62 is executed so as to be electrically conductive, for example metallic, in order to assist the electrode function of the media system in a particularly efficient way. In view of a desired high biocompatibility, particularly promoting the use in the treatment of patients, the media distribution ring 62 is preferably made from titanium grade 5.

Furthermore, the media channel 66 and in particular also the media distribution ring 62 are provided on their inner surfaces with a metallic coating 70, which in the exemplary embodiment is made from aluminum and/or magnesium. This coating 70 offers, on the one hand, in a particularly reliable manner the desired electrical conduction properties for the media-supply system, so that the latter can be used in a particularly simple and reliable manner as a counter-electrode. In order to particularly promote, in addition, also the execution of the distribution element 52 as a through-away product, the metallic coating 70 is designed as a metallic sacrificial coating, for example by suitably choosing the thickness of the coating. This design means that during use of the distribution ring 52, i.e. the feeding of the cleaning fluid and, at the same time, electrical charging with current in operation, the metallic components of the sacrificial coating electrochemically dissolve in the cleaning fluid fed, thus enriching the latter with metal ions which particularly promote the process of cleaning the post part or first dental implant part 2 and charging it with current.

As soon as this metallic coating 70 designed as a sacrificial coating has been removed as a consequence of this electrochemical dissolution due to the treatment, only the basic material of the fluid distribution ring 62 or of the media channel 66 is in contact with the cleaning fluid carried therein, and the electrochemical activity of the system is considerably reduced. If the operating parameters (for example current density, temperature, composition of the cleaning fluid) are suitably chosen, the distribution element 52 can, therefore, no longer be used after complete removal of the sacrificial coating, and, therefore, the distribution element 52 can be designed in a particularly favorable manner for a one-time use for the treatment of a patient.

The cleaning system 30 is particularly preferably provided for a treatment of the dental implant part 2 using a cleaning fluid, as it is known, with regard to its components and variants, from DE 10 2012 022 593. Particularly good and, therefore, advantageous cleaning results can be achieved by a combined application of such a cleaning fluid with additional charging of the dental implant part 2 with current. Due to the execution of the metallic coating as a sacrificial coating, in which a corresponding input of ions into the electrolyte fed is effected, a cleaning fluid designed in the manner of an in-situ generation during the process control properly speaking can be generated. In a particularly preferred use of the cleaning system 30, which is considered as independently inventive, an electrolyte comprising citric acid, lactic acid, malic acid and/or ethanoic acid, is supplied to the distribution element 52. This particularly preferred combined use of the electrolyte with the cleaning system 30 creates, through the input of ions from the sacrificial coating into the electrolyte, the treating and cleaning fluid, which is actually effective in the inserted region of the implant 2 and which comprises, in addition to the above-mentioned fractions of acids, the fraction of ions from magnesium, aluminum, manganese, zinc, and/or copper, and is known, with regard to its components and variants, from DE 10 2012 022 593. Especially a cleaning fluid comprising these components has surprisingly turned out to be particularly reliable and effective in the treatment of the inserted implant part. Preferably, the electrolyte supplied to the distribution element 52 can also contain from the start additional fractions of a metal salt comprising magnesium, aluminum, potassium and/or calcium ions.

In principle, the components of the cleaning system 30 which are intended for carrying current are in the exemplary embodiment made from titanium, preferably pure titanium (grade 1 to 4), as basic material, because this can be applied for the above-mentioned purposes in a particularly reliable manner, thanks to its high biocompatibility. In order to guarantee in this case in a simple manner a particularly high safety of operation, also in view of the preferably provided execution as a through-away product, these components are in addition provided with a water-soluble outer coating 72, made, for example, of sugar, in the manner of an encapsulated design, which outer coating 72 dissolves when it gets into contact with the cleaning fluid or a body fluid, exposing the electrode material properly speaking. The outer coating 72 is applied in this case directly on the basic material or, if necessary, also on the metallic coating 70 provided thereon, in the manner of a stack of layers.

Figure 5A:
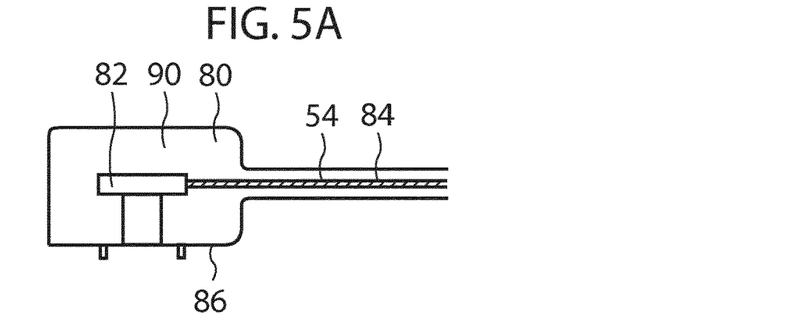

The inner structure of the contact element 50 is clearly recognizable in the representations of FIG. 5. FIG. 5A is a longitudinal sectional view of the contact element 50. The contact element 50 comprises an external housing body 80, which is preferably made from a synthetic material or another electrically insulating material. In the housing head 80, an electrically conductive, preferably metallic, contact clamping ring 82 is integrated, which is connected to an electrical conductor element 84 forming the power supply line 54 and leading outwards. The contact clamping ring 82 is of an annular design and is dimensioned such that it can suitably be pushed onto the base body 34 of the securing element 32. A number of plug elements 88 are formed onto the bottom end face 86 of the housing head 80, which plug elements 88 can engage into corresponding suitably designed sockets located on the top side of the distribution element 52. In the multi-part design of the cleaning system 30, the contact element 50 can, therefore, be connected with the distribution element 52 in an engaging manner by attaching it to the securing element 32.

Figure 5B:
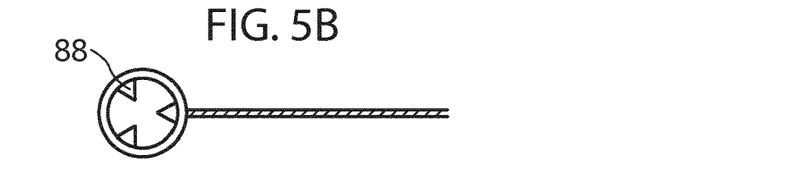

As can be seen in the cross-sectional view of FIG. 5B, a number of contacting tips 88 facing inwardly are formed onto the contact clamping ring 82. When the contact element 50 is attached to the securing element 32, these contacting tips 88 penetrate the coating applied on the base body 34, thus ensuring a reliable electrical connection of the contact clamping ring 82 to the base body 34 of the securing element 32. Furthermore, the contacting tips 88 are designed such, regarding the choice of their material and dimensioning, that they deform themselves and/or bend when being attached to the securing element 32. In this way, it is recognizable after use of the contact element 50 that the latter has already been used, so that the execution as a through-away product is particularly promoted.

In order to further promote the use as a through-away product, the central upper region 90 of the housing head 80 is designed as a penetrable seal. This design is based on the concept that the cleaning system 30 shall be assembled in such a manner that first of all, the securing element 32 is screwed onto the post part or first dental implant part 2 and then the distribution element 52 and the contact element 50 are attached thereto in an engaging manner. When disassembling the cleaning system 30, the seal located in the central upper region 90 of the housing head 80 shall then be penetrated by a suitable tool, for example a screw driver, so that the tool can engage into a corresponding groove 92 in the head region of the base body 34 of the securing element 32.

Figure 6A:
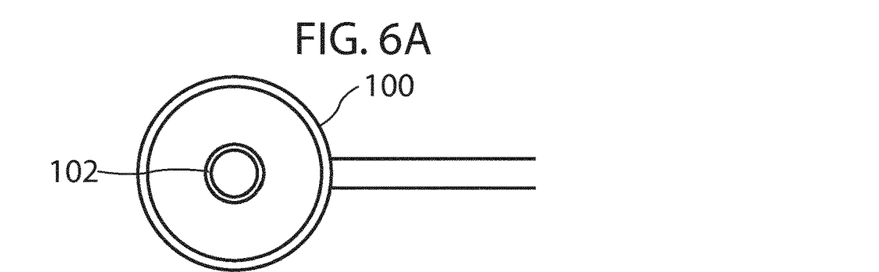
Figure 6B:
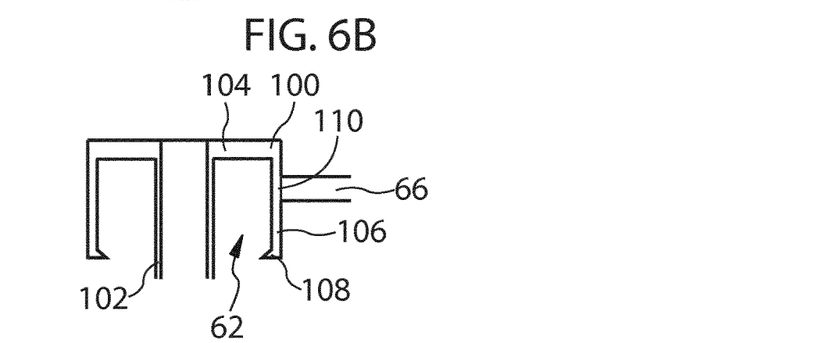
Figure 7:
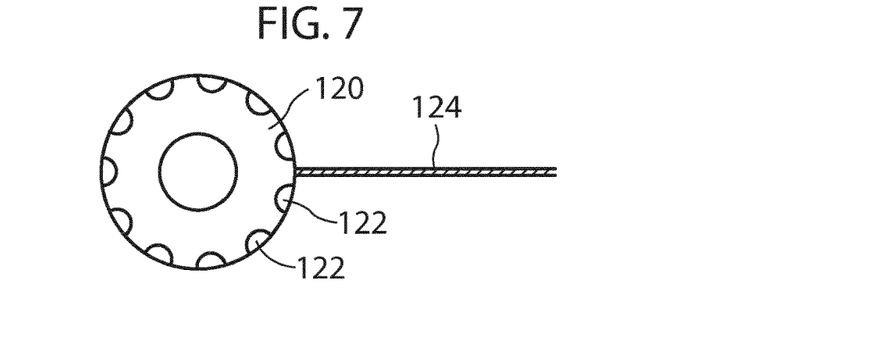
FIG. 7 is a top view of a distributor insert of the distribution element according to FIG. 6.

In this way, the securing element 32 together with the component contact element 50 attached thereto and the distribution element 52 can be screwed out of the thread 20 of the post part by means of the tool. The penetration of the seal necessary for this purpose ensures that the contact element 50 is suited for a one-time use only and is thus executed as a through-away product. In order to further promote this design, the distribution element 52 is in the exemplary embodiment also a multi-component part, as can be seen in FIG. 6 and FIG. 7. The distribution element 52, for its part, comprises for this purpose a housing cap 100 made from an electrically insulating material, preferably a synthetic material.

As can be seen in the cross-sectional view of FIG. 6A and in the longitudinal sectional view of FIG. 6B, the housing cap 100, for its part, is of an annular structure and comprises an inner cylinder jacket 102 that can be pushed onto the base body 34 of the securing element 32. A projecting cover ring 104 is formed onto the upper end of the cylinder jacket 102, the outer region of said projecting cover ring 104 transitions into an external cylinder jacket 106 enclosing the cylinder jacket 102 in an annular manner. The lower end of the external cylinder jacket 106 terminates in a peripheral detent collar 108 which engages onto the peripheral annular bead 40 of the securing element 32, when the housing cap 100 is attached to the securing element 32. Thus, in attached state, the cylinder jackets 102, 106 together with the cover ring 104 and the annular bead 40 form the ring channel 62 of the distribution element 52, which on the media side is connected via a passage opening 110 to the media channel 66 formed onto the external cylinder jacket 106.

A fluid distributor 120, preferably made from an electrically conductive material, shown in FIG. 7 in a cross-sectional view, which in its outer region is provided with a number of notches 122, which in the assembled state correspond with the outlet openings 64 for a purposeful distribution of the cleaning fluid, is inserted into the clearance between the inner cylinder jacket and the outer cylinder jacket 106, that is provided for forming the ring channel 62. The distributor ring 120 can in the exemplary embodiment be connected to the external power source in an electrically conductive manner by means of a power cable 124.

LIST OF REFERENCE NUMBERS

1 Dental implant system
2, 4 Dental implant part
6 External thread
8 Apical end
10 Connection stud
12 Receiving channel
18 Connecting screw
20 Screw thread
30 Cleaning system
32 Securing element
34 Base body
36 End of the base body 34
38 External thread of the base body 34
40 Annular bead
42 Electrically insulating surface coating
50 Contact element
52 Distribution element
54 Power supply line
56 Contact head
60 External housing of the distribution element 52
62 Media ring channel/media distribution ring/ring channel
64 Media outlet opening of the media ring channel 62
66 Media channel
70 Metallic coating
72 External coating
80 Housing body
82 Contact clamping ring
86 End face 88 Plug element
90 Central upper region of the housing head 80
92 Groove
100 Housing cap of the distribution element 52
102 Cylinder jacket of the housing cap 100
104 Cover ring of the cylinder jacket 104
106 External cylinder jacket
108 Detent collar of the external cylinder jacket 106
110 Passage opening of the ring channel 62
120 Fluid distributor
122 Notches of the fluid distributor 120
124 Power cable

What is claimed is:

1. A cleaning system (30) for a dental implant part (2) that has been introduced into the jaw bone of a patient, comprising
a securing element (32) having a connection end that is capable of being received by a connection element in the dental implant part (2) and a plug-type connection end,
a distribution element (52), which is capable of being connected to an external media reservoir via a media channel (66), said distribution element (52) having a media outlet opening (64) at its periphery, and
an electrical contact element (50), which is capable of being connected to an external power source via a power supply line (54), said electrical contact element (50) is capable of being electrically connected to the dental implant part (2),
wherein both the distribution element (52) and the electrical contact element (50) are removably plugged in or slipped on the plug-type connection end, the electrical contact element (50) is removably secured over the distribution element (52), the distribution element (5452) is removably seated upon the securing element (32), and
wherein, when the electrical contact element (50) is removably secured over the distribution element (52) and the distribution element (5452) is removably seated upon the securing element (32), the media channel (66) is connectable to the external media reservoir.

2. The cleaning system (30) of claim 1, whose securing element (32) includes an electrically conductive base body (34), which is provided with an electrically insulating surface coating (42).

3. The cleaning system (30) of claim 1, whose distribution element (52) includes a media ring channel (62) having a number of media outlet openings (64), which is connectable on a media side to the media channel (66).

4. The cleaning system (30) of claim 1, whose distribution element (52) includes an electrically insulating external housing (60).

5. The cleaning system (30) of claim 1, in whose media channel (66) a power cable (124) is integrated.

6. The cleaning system (30) of claim 1, wherein the distribution element (52) and/or the electrical contact element (50) are capable of being removed after use and thrown away.

7. The cleaning system (30) of claim 3, wherein the media channel (66) and/or the media ring channel (62) has a channel surface that is provided with a metallic coating (70).

8. The cleaning system (30) of claim 4, wherein the electrically insulating external housing (60) of the distribution element (52) includes a detent collar (108) which can be attached to a corresponding peripheral bead (40) of the securing element (32).

9. The cleaning system (30) of claim 1, whose electrical contact element (50) includes a contact clamping ring (82) which is connected in an electrically conductive manner with the power supply line and which is provided with a number of contacting points.

10. The cleaning system (30) of claim 1, whose contact element (50), distribution element (52) and/or securing element (32) are provided totally or partially with a water-soluble external coating (72).

11. The cleaning system (30) of claim 2, wherein the electrically conductive base body (34) is metallic.

12. The cleaning system (30) of claim 7, wherein the metallic coating (70) comprises magnesium and/or aluminum.

13. The cleaning system (30) of claim 10, wherein the water-soluble external coating (72) comprises sugar.

14. The cleaning system (30) of claim 7, wherein the metallic coating (70) is a source of metal ions during operation of the cleaning system (30).

15. The cleaning system (30) of claim 1, wherein the distribution element (52) and the electrical contact element (50) are capable of being attached to and removed from the securing element (32) after the securing element (32) has been received by the connection element.

16. The cleaning system (30) of claim 1, wherein the securing element (32) forms an axis and the distribution element (52) is attached around the securing element (32) and the electrical contact element (50) is attached to the securing element (32) above the distribution element (52).

17. The cleaning system (30) of claim 1, wherein the distribution element (52) and the electrical contact element (50) are slipped on the securing element (32).

18. The cleaning system (30) of claim 1, wherein the connection end has a screw thread that is capable of being screwed into the connection element.

19. The cleaning system (30) of claim 1, wherein the base body (34) comprises a media through-channel to the receiving channel (12) of the dental implant part (2).

20. A cleaning system (30) for a dental implant part (2) that has been introduced into the jaw hone of a patient, comprising
a securing element (32) having a connection end that is capable of being removably attached to a connection element in the dental implant part (2) and having a plug type connection end,
a distribution element (52) capable of being connected to an external media reservoir via a media channel (66), and
an electrical contact element (50) capable of being connected to an external power source via a power supply line (54), said electrical contact element (50) is capable of being electrically connected to the dental implant part (2),
wherein the distribution element (52) and the electrical contact element (50) are capable of being removably plugged in or slipped on the plug-type connection end of the securing element (32) when the securing element (32) is attached to the connection element,
wherein the media channel (66) comprises a metallic sacrificial coating, and
wherein the electrical contact element (50) is removably secured over the distribution element (52) and the distribution element (52) is removably seated upon the securing element (32), and the media channel (66) is connectable to the external media reservoir.

21. The cleaning system (30) of claim 20, wherein the electrical contact element (50) is capable of being attached to and removed from the securing element (32) when the distribution element (52) is attached to the securing element (32).

\* \* \* \* \*